(12) United States Patent
Andéchaga et al.

(10) Patent No.: US 9,114,165 B2
(45) Date of Patent: Aug. 25, 2015

(54) PHARMACEUTICAL COMPOSITION OF IBUPROFEN FOR INJECTION

(75) Inventors: Ignacio Ortúzar Andéchaga, Madrid (ES); Mario Ortúzar Gutiérrez, Madrid (ES)

(73) Assignee: Spain Pharma S.A., Madrid (ES)

( * ) Notice: Subject to any disclaimer, the term of this patent is extended or adjusted under 35 U.S.C. 154(b) by 281 days.

(21) Appl. No.: 13/641,921

(22) PCT Filed: May 18, 2011

(86) PCT No.: PCT/EP2011/058087
§ 371 (c)(1),
(2), (4) Date: Nov. 6, 2012

(87) PCT Pub. No.: WO2011/144677
PCT Pub. Date: Nov. 24, 2011

(65) Prior Publication Data
US 2013/0231390 A1    Sep. 5, 2013

(30) Foreign Application Priority Data

May 18, 2010   (WO) ................. PCT/ES2010/070330

(51) Int. Cl.
A61K 47/18   (2006.01)
A61K 31/192  (2006.01)
A61K 9/00    (2006.01)
A61K 31/19   (2006.01)

(52) U.S. Cl.
CPC .............. A61K 47/18 (2013.01); A61K 9/0019 (2013.01); A61K 31/19 (2013.01); A61K 31/192 (2013.01)

(58) Field of Classification Search
CPC ..... A61K 31/19; A61K 31/192; A61K 47/18; A61K 9/0019
USPC .................... 514/570, 440; 549/39
See application file for complete search history.

(56) References Cited

U.S. PATENT DOCUMENTS

2008/0153915 A1*   6/2008   Veronesi ...................... 514/568

FOREIGN PATENT DOCUMENTS

EP   19912436   *  3/1999 ............. A61K 31/19

* cited by examiner

Primary Examiner — Savitha Rao
(74) Attorney, Agent, or Firm — Ladas & Parry LLP

(57) ABSTRACT

Pharmaceutical composition of ibuprofen for injection that comprises an aqueous solution of ibuprofen and trometamol. These compositions display a minimal loss of active principle and acceptable increase of impurities after autoclaving, properties that have been demonstrated in various types of containers, such as containers made of plastics such as polypropylene, PVC and polyethylene, as well as in glass containers. These compositions, after undergoing autoclaving, still comply with all the relevant technical specifications of the European Pharmacopoeia and of the USP.

14 Claims, No Drawings

PHARMACEUTICAL COMPOSITION OF IBUPROFEN FOR INJECTION

RELATED APPLICATION INFORMATION

This application is a 371 of International Application PCT/EP2011/058087 filed 18 May 2011 entitled "Pharmaceutical Composition Of Ibuprofen For Injection", which was published on 24 Nov. 2011, with International Publication Number WO 2011/144677 A1, and which claims priority from International Application No. PCT/ES2010/070330 filed 18 May 2010, the contents of which are incorporated herein by reference.

FIELD OF THE INVENTION

The present invention relates to a pharmaceutical composition for intravenous use that comprises 2-(4-isobutylphenyl)-propionic acid (ibuprofen), trometamol and NaCl.

BACKGROUND OF THE INVENTION 2-(4-Isobutylphenyl)-propionic acid (ibuprofen) is an analgesic, antipyretic, anti-inflammatory drug that has the following chemical formula:

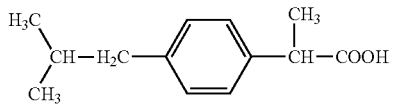

Ibuprofen is a drug that has become very well known since its invention in the 1960s, and is currently marketed for the treatment of pain, inflammation and fever, under a variety of trade names in pharmaceutical forms for oral administration.

Ibuprofen can be in the form of the (R) or (S) enantiomers, and although it is the (S) enantiomer that is biologically active, the majority of preparations contain the racemic mixture, since the (R) enantiomer is converted to the active form (S) in vivo. Hereinafter, "ibuprofen" is to mean either of the two enantiomers, (R) or (S), or the racemate.

Despite its many advantages, one of the main drawbacks of ibuprofen is, however, its poor solubility in water. Ibuprofen is a monoprotic acid with pKa=4.4. Its solubility is therefore closely related to pH, and may vary from 78 micrograms/mL at acidic pHs to 291 mg/mL at alkaline pHs. As a result, the development of certain dosage forms of ibuprofen, in particular liquid dosage forms for injection, has been problematic.

Thus, for example, international publications WO 03/039532 A1 and WO 2005/065674 A1 describe liquid pharmaceutical compositions of ibuprofen that include amino acids such as arginine for improving the solubility of ibuprofen, and that have pH values below 7.8. However, these formulations have the drawback that, although they can be submitted to thermal treatment up to a certain degree, they cannot be autoclaved since in the conditions of autoclave sterilization, i.e. generally for 15 minutes at 121° C., the arginine would decompose, generating unforeseeable impurities. This means that such formulations cannot be submitted to the aforesaid autoclaving procedure, which is the method of sterilization that must be used as first choice and is the most advisable for any injectable pharmaceutical formulation.

An injectable pharmaceutical composition of ibuprofen is already marketed with the trade name Caldolor, with composition according to the formulation described in the international publications cited above, and which is indicated for the treatment of moderate to severe pain and for fever. This formulation contains, per 1 mL of solution, 100 mg of ibuprofen in water for injection (therefore at a concentration of 100 mg/mL of ibuprofen) and 78 mg of arginine, at arginine:ibuprofen molar ratio of 0.92:1, in glass vials that contain 400 or 800 mg of ibuprofen, and at a pH of about 7.4. This formulation, however, is very concentrated for direct use and requires subsequent dilution to 100 or 200 millilitres. Moreover, as already mentioned, it cannot be autoclaved, thus necessitating very expensive aseptic manufacture.

Pharmaceutical formulations for parenteral use that contain ibuprofen at a concentration of 8 mg/mL and trometamol (tris-hydroxymethyl-aminomethane) at a concentration of 6.04 mg/mL, the pH being limited to the range 7.8-8.2, are also known from DE 199 12 436 A1 and its subsequent international publication WO 00/56325. However, this document neither describes nor suggests formulations with other values of concentration of the stated components, or with pH values outside of the stated range. In addition, the relatively high content of ibuprofen in the compositions disclosed in this document may compromise the solubility of ibuprofen at the pH of the composition, and the additional fact that the sterilization of these compositions was carried out by sterile filtration suggests that these compositions were possibly not suitable for sterilization in autoclave. This unsuitability has anyway been demonstrated through comparative experimental tests reported hereinbelow.

SUMMARY OF THE INVENTION

Accordingly, the problem to be solved by the present invention is to provide injectable liquid formulations of ibuprofen that overcome the drawbacks of the compositions disclosed in the prior art, and in particular that permit autoclaving with minimal loss of ibuprofen and production of impurities and other parameters of pharmaceutical interest that remain within the acceptable limits in the pharmacopoeia after the autoclaving process. Although a certain number of formulations of ibuprofen are described in the prior art, there is, however, the difficulty that none of them can be autoclaved, as their formulation includes compounds that degrade during autoclaving, giving rise to unforeseeable impurities, which rules them out for use for injection.

The solution to this problem is based on the fact that the inventors have found that liquid compositions of ibuprofen in which this active principle is at a concentration of between 2 and 6 mg/mL, and preferably approximately 4 mg/mL, that comprise trometamol at a concentration of between 1.8 and 5.8 mg/ml and that have a pH above 7, and preferably from 8.0 to 9.0, surprisingly can be autoclaved with a minimal loss of active principle and a low increase of impurities that remain within acceptable limits, so that they are particularly suitable for use as an injectable pharmaceutical formulation. The aforementioned properties of these formulations, so that they can be autoclaved, displaying minimal loss of active principle and acceptable production of impurities after autoclaving, have been demonstrated in different types of containers, such as containers made of plastic such as polypropylene (PP), PVC or polyethylene, though also in glass containers, although to a varying extent in each of them.

Therefore a first aspect of the invention relates to a pharmaceutical composition of ibuprofen for injection that comprises an aqueous solution of ibuprofen and trometamol, in which the concentration of ibuprofen is between 2 and 6 mg/mL, and preferably about 4 mg/mL, the trometamol is at a concentration of between 1.8 and 5.8 mg/ml, and preferably about 3.8 mg/ml, and the pH of said composition is between 7.0 and 9.5. These compositions are useful in the treatment of pain, inflammation or fever.

In a second aspect, the invention relates to the use of said compositions in the manufacture of a medicinal product for the treatment of pain, inflammation or fever.

DETAILED DESCRIPTION OF THE INVENTION

The liquid pharmaceutical compositions of the invention therefore comprise ibuprofen at a concentration between and 6 mg/ml, and preferably of about 4 mg/ml, trometamol at a concentration between 1.8 and 5.8 mg/ml, preferably about 3.8 mg/ml, and the necessary NaCl to provide suitable isotonicity that is usually about 300 mOsm/kg, which requires a concentration of NaCl preferably of about 7.7 mg/ml. It is believed that the trometamol aids in increasing the dissolution rate of ibuprofen in the aqueous solvent and also helps in maintaining the stability of ibuprofen in solution. In the compositions of the invention, the trometamol is added at a concentration of between 1.5 and 5.8 mg/ml, and preferably about 3.8 mg/ml. The pH of the compositions of the invention is between 7.0 and 12, preferably between 7.0 and 9.5, more preferably between 7.5 and 9.0, even more preferably between 8.0 and 9.0, and most preferably about 8.5, depending on the container in which they are presented. The pH can be adjusted by any means known by a person skilled in the art for carrying out said adjustment, although preferably it will be done with NaOH/HCl until the desired pH is reached.

Throughout the present specification, "autoclaving" means any thermal method that makes sterilization of the formulation possible, and in particular a procedure during which the formulations are submitted to a temperature between 110 and 130° C. for a time of 2 to 190 minutes, and more particularly to a temperature between 120 and 125° C. for a time of 15 to 20 minutes.

Also throughout the present specification, it will be understood that a solution for injection is sterilizable by heat or "autoclavable" when, after undergoing an autoclaving procedure according to the preceding paragraph, its content in ibuprofen is at least 95% of the initial ibuprofen content added to the solution.

Experimental Tests

Various experimental tests of formulation and autoclaving of ibuprofen were carried out, in various packaging materials: polyethylene (PE), glass, polyvinyl chloride (PVC) and polypropylene (PP), at various pH values. In this connection, it must be pointed out that, throughout the present specification, when reference is made to the packaging material for the compositions of the invention, this is to be understood as the material that is in direct contact with said compositions. Obviously, the containers that contain the compositions according to the invention can be composed of layers of different materials, so that the layers that are not in direct contact with the compositions according to the invention can have a different composition from that indicated.

The formulation used was as follows:
Ibuprofen base BASF: 4 mg/ml
Trometamol Merck: 3.8 mg/ml
NaCl Esco: 7.7 mg/ml In order to prepare the compositions used in the following experimental tests, the excipients were first added to water at the temperature of 50° C. Then the ibuprofen was added under stirring, and after about one hour of stirring the ibuprofen was completely dissolved. Finally, the pH was adjusted to the desired value using HCl 1N and/or NaOH 1N, depending on the case.

With this base formulation, samples were prepared at the following values of pH: 6.5, 7.0, 7.5, 7.8, 8.0, 8.2, 8.5, 9.0 and 9.5. Each of these formulations was packaged in glass containers, bags of polypropylene (PP), bags of PVC and containers of low density polyethylene. In the autoclaving tests, the glass containers, the polypropylene bags and the PVC bags were autoclaved at 121° C. for 15 minutes, as specified by the conditions of the European Pharmacopoeia for this process. The polyethylene containers were autoclaved at 110° C. for 3 hours. In parallel, a series of comparative compositions was prepared in the same conditions as the above but using the formulation disclosed in DE 199 12 436 A1, namely:
Ibuprofen base BASF: 8 mg/mL
Trometamol Merck: 6.05 mg/mL
NaCl Esco: 5.4 mg/mL In this case, the compositions were adjusted to the following pH values: 7.8, 8.2 and 9.0, and were tested only in 100 mL capacity containers of different materials.

The results obtained were as follows:

1) Investigation of the Content of Impurities in the Test Formulations after Autoclaving:

Determination of impurities was carried out by analysis by HPLC using the following parameters:

Mobile phase: For preparation of the mobile phase, 3 ml of ammonia was dissolved in 1920 ml of water, adjusting to pH=2.5 with phosphoric acid; then 1080 ml of acetonitrile was added.
Flow: 2.3 ml/min.
Column: C18, 150 mm×4.6 mm, 5 μm.
Detection: 214 nm.
Volume injected: 10 μl.
Temperature=25° C.
Duration=40 minutes.
Test sample: Direct injection.
Reference sample: Standard solution of ibuprofen in mobile phase at a concentration of 0.04 mg/ml (1.0% relative to the test sample).
Suitability solution: Contains 4 μg/ml of impurity B and 4 mg/ml of ibuprofen.
Suitability criterion: The resolution between ibuprofen and impurity B is greater than 2.

The results obtained for the various formulations in the various containers were as shown in the following tables, in which the impurities are indicated by their corresponding retention time (Trr) in the HPLC test and, when said impurity has been identified, they also show the letter (A, J, N, etc.) that defines said impurity according to the corresponding analysis certificate according to the European Pharmacopoeia:

| | pH 6.5: Impurities (%) | | | | | | | |
|---|---|---|---|---|---|---|---|---|
| | Without Autoclaving | | | | Autoclaved | | | |
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | 0.01 | 0.01 | 0.01 | 0.01 |
| 0.31 (Imp N) | 0.06 | 0.06 | 0.06 | 0.06 | 0.06 | 0.06 | 0.06 | 0.06 | pH 6.5: Impurities (%)

| | | | | | | | | |
|---|---|---|---|---|---|---|---|---|
| 0.58 | 0.02 | 0.02 | 0.02 | 0.02 | 0.02 | 0.01 | 0.02 | 0.02 |
| 0.93 (Imp A) | 0.02 | 0.02 | 0.02 | 0.02 | 0.02 | 0.02 | 0.02 | 0.02 |
| 1.83 | ND | ND | ND | ND | 0.05 | 0.03 | 0.04 | ND |
| Total | 0.10 | 0.10 | 0.10 | 0.10 | 0.16 | 0.13 | 0.15 | 0.11 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | 0.01 | 0.02 |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.11 | 0.12 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | 0.02 | 0.02 |
| 0.31 (Imp N) | 0.06 | 0.06 | 0.06 | 0.06 |
| 0.58 | 0.02 | 0.02 | 0.01 | 0.02 |
| 0.93 (Imp A) | 0.02 | 0.02 | 0.02 | 0.02 |
| 1.83 | ND | ND | ND | ND |
| Total | 0.10 | 0.10 | 0.11 | 0.12 |

It can be seen that in the samples packaged in containers of glass and of PE, the total content of impurities changes, on average, from approximately 0.10% before autoclaving to 0.12% after autoclaving, whereas in those kept in containers of PVC and PP it changes from approximately 0.10% to 0.15%, and is in all cases below the reference value of 0.20%.

pH 7.0: Impurities (%)

| | Without Autoclaving | | | | Autoclaved | | | |
|---|---|---|---|---|---|---|---|---|
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | 0.01 | 0.01 | 0.01 | 0.01 |
| 0.31 (Imp N) | 0.06 | 0.06 | 0.06 | 0.06 | 0.06 | 0.06 | 0.06 | 0.06 |
| 0.58 | 0.02 | 0.02 | 0.02 | 0.02 | 0.02 | 0.01 | 0.02 | 0.02 |
| 0.93 (Imp A) | 0.02 | 0.02 | 0.02 | 0.02 | 0.02 | 0.02 | 0.02 | 0.02 |
| 1.83 | ND | ND | ND | ND | 0.06 | 0.04 | 0.03 | ND |
| Total | 0.10 | 0.10 | 0.10 | 0.10 | 0.17 | 0.14 | 0.14 | 0.11 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | 0.02 | 0.02 |
| 0.31 (Imp N) | 0.06 | 0.06 | 0.06 | 0.06 |
| 0.58 | 0.02 | 0.02 | 0.02 | 0.02 |

-continued

| | pH 7.0: Impurities (%) | | | |
|---|---|---|---|---|
| 0.93 (Imp A) | 0.02 | 0.02 | 0.02 | 0.02 |
| 1.83 | ND | ND | ND | ND |
| Total | 0.10 | 0.10 | 0.12 | 0.12 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | 0.02 | 0.02 |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.12 | 0.12 |

Once again it can be seen that in the samples packaged in containers of glass and of PE, the total content of impurities changes, on average, from approximately 0.10% before autoclaving to 0.12% after autoclaving, whereas in those kept in containers of PVC and PP it changes from approximately 0.10% to 0.15%, and is in all cases below the reference value of 0.20%.

| | pH 7.5: Impurities (%) | | | | | | | |
|---|---|---|---|---|---|---|---|---|
| | Without Autoclaving | | | | Autoclaved | | | |
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | ND | 0.01 | 0.01 | 0.01 |
| 0.31 (Imp N) | 0.06 | 0.06 | 0.06 | 0.06 | 0.06 | 0.06 | 0.06 | 0.06 |
| 0.58 | 0.02 | 0.02 | 0.02 | 0.02 | 0.02 | 0.02 | 0.02 | 0.02 |
| 0.93 (Imp A) | 0.02 | 0.02 | 0.02 | 0.02 | 0.02 | 0.02 | 0.02 | 0.02 |
| 1.83 | ND | ND | ND | ND | 0.05 | 0.03 | 0.04 | ND |
| Total | 0.10 | 0.10 | 0.10 | 0.10 | 0.15 | 0.13 | 0.15 | 0.11 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | 0.01 | 0.01 |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.11 | 0.11 | pH 7.5: Impurities (%)

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | 0.02 | 0.02 |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.12 | 0.12 |

It is also observed at this pH that, in the samples packaged in containers of glass and of PE, the total content of impurities changes from approximately 0.10% before autoclaving to 0.12% after autoclaving, whereas in those kept in containers of PVC and PP it changes from approximately 0.10% to 0.15%, and is in all cases below the reference value of 0.20%.

pH 8.0: Impurities (%)

| | Without Autoclaving | | | | Autoclaved | | | |
|---|---|---|---|---|---|---|---|---|
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | ND | ND | ND | ND |
| 0.31 (Imp N) | 0.06 | 0.06 | 0.06 | 0.06 | 0.06 | 0.06 | 0.06 | 0.06 |
| 0.58 | 0.01 | 0.02 | 0.02 | 0.01 | 0.02 | 0.02 | 0.02 | 0.02 |
| 0.93 (Imp A) | 0.02 | 0.02 | 0.02 | 0.02 | 0.02 | 0.02 | 0.02 | 0.02 |
| 1.83 | ND | ND | ND | ND | 0.03 | ND | 0.03 | ND |
| Total | 0.09 | 0.10 | 0.10 | 0.09 | 0.13 | 0.10 | 0.13 | 0.10 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | 0.01 | 0.01 |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.11 | 0.11 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | 0.01 | ND |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.11 | 0.10 |

In this case we observe a smaller increase in the resultant level of impurities after autoclaving, since, in the samples packaged in containers of glass and of PE, the total content of impurities changes on average from approximately 0.10% before autoclaving to 0.11% after autoclaving, whereas in those kept in containers of PVC and PP it changes on average from approximately 0.10% to 0.12%, and is in all cases below the reference value of 0.20%.

| | pH 8.5: Impurities (%) | | | | | | | |
|---|---|---|---|---|---|---|---|---|
| | Without Autoclaving | | | | Autoclaved | | | |
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | ND | ND | ND | ND |
| 0.31 (Imp N) | 0.06 | 0.06 | 0.06 | 0.06 | 0.06 | 0.06 | 0.06 | 0.06 |
| 0.58 | 0.02 | 0.01 | 0.02 | 0.01 | 0.02 | 0.02 | 0.02 | 0.01 |
| 0.93 (Imp A) | 0.02 | 0.02 | 0.02 | 0.02 | 0.02 | 0.02 | 0.02 | 0.02 |
| 1.83 | ND | ND | ND | ND | 0.02 | 0.03 | 0.04 | 0.01 |
| Total | 0.10 | 0.09 | 0.10 | 0.09 | 0.12 | 0.13 | 0.14 | 0.10 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | ND | ND |
| 0.31 (Imp N) | 0.06 | 0.06 | 0.06 | 0.06 |
| 0.58 | 0.01 | 0.02 | 0.02 | 0.02 |
| 0.93 (Imp A) | 0.02 | 0.02 | 0.02 | 0.02 |
| 1.83 | ND | ND | ND | ND |
| Total | 0.09 | 0.10 | 0.10 | 0.10 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | ND | ND |
| 0.31 (Imp N) | 0.06 | 0.06 | 0.06 | 0.06 |
| 0.58 | 0.01 | 0.02 | 0.02 | 0.02 |
| 0.93 (Imp A) | 0.02 | 0.02 | 0.02 | 0.02 |
| 1.83 | ND | ND | ND | ND |
| Total | 0.09 | 0.10 | 0.10 | 0.10 |

In the present case with pH 8.5, the trend already observed at pH 8.0 appears to be maintained, namely observation of a smaller increase in the level of impurities after autoclaving, since in the samples packaged in containers of glass and of PE, the total content of impurities changes, on average, from approximately 0.10% before autoclaving to 0.11% after autoclaving, whereas in those kept in containers of PVC and PP it changes on average from approximately 0.10% to 0.13%, and is in all cases below the reference value of 0.20%.

| | pH 9.0: Impurities (%) | | | | | | | |
|---|---|---|---|---|---|---|---|---|
| | Without Autoclaving | | | | Autoclaved | | | |
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | ND | ND | ND | ND |

-continued

| | pH 9.0: Impurities (%) | | | | | | | |
|---|---|---|---|---|---|---|---|---|
| 0.31 (Imp N) | 0.06 | 0.06 | 0.06 | 0.06 | 0.06 | 0.06 | 0.06 | 0.06 |
| 0.58 | 0.02 | 0.02 | 0.06 | 0.01 | 0.02 | 0.02 | 0.02 | 0.02 |
| 0.93 (Imp A) | 0.02 | 0.02 | 0.06 | 0.02 | 0.02 | 0.02 | 0.02 | 0.03 |
| 1.83 | ND | ND | ND | ND | 0.01 | ND | 0.04 | 0.02 |
| Total | 0.10 | 0.10 | 0.18 | 0.09 | 0.11 | 0.10 | 0.14 | 0.13 |

| | Without Autoclaving | | Autoclaved | |
|---|---|---|---|---|
| Trr | Glass 100 ml | Glass 200 ml | Glass 100 ml | Glass 200 ml |
| 0.20 | ND | ND | ND | ND |
| 0.31 (Imp N) | 0.06 | 0.06 | 0.06 | 0.06 |
| 0.58 | 0.02 | 0.02 | 0.02 | 0.01 |
| 0.93 (Imp A) | 0.02 | 0.02 | 0.02 | 0.02 |
| 1.83 | ND | ND | ND | ND |
| Total | 0.10 | 0.10 | 0.10 | 0.09 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | ND | ND |
| 0.31 (Imp N) | 0.06 | 0.06 | 0.06 | 0.06 |
| 0.58 | 0.02 | 0.01 | 0.01 | 0.02 |
| 0.93 (Imp A) | 0.02 | 0.02 | 0.02 | 0.02 |
| 1.83 | ND | ND | ND | ND |
| Total | 0.10 | 0.09 | 0.09 | 0.10 |

At pH 9.0 it appears that the previous trend is still maintained, since in the samples packaged in containers of glass and of PE, the total content of impurities remains practically constant after autoclaving, whereas in those kept in containers of PVC and PP it increases slightly, on average from approximately 0.10% to 0.12%, and is in all cases below the reference value of 0.20%.

| | pH 9.5: Impurities (%) | | | | | | | |
|---|---|---|---|---|---|---|---|---|
| | Without Autoclaving | | | | Autoclaved | | | |
| Trr | PVC 100 ml | PVC 200 ml | PP 100 ml | PP 200 ml | PVC 100 ml | PVC 200 ml | PP 100 ml | PP 200 ml |
| 0.20 (Imp J) | ND | ND | ND | ND | ND | ND | ND | ND |
| 0.31 (Imp N) | 0.06 | 0.06 | 0.06 | 0.06 | 0.06 | 0.06 | 0.06 | 0.06 |
| 0.58 | 0.01 | 0.02 | 0.02 | 0.01 | 0.02 | 0.02 | 0.01 | 0.02 |
| 0.93 (Imp A) | 0.02 | 0.02 | 0.02 | 0.02 | 0.02 | 0.02 | 0.02 | 0.02 |
| 1.83 | ND | ND | ND | 0.01 | ND | 0.03 | 0.02 | |
| Total | 0.09 | 0.10 | 0.10 | 0.09 | 0.11 | 0.10 | 0.12 | 0.12 |

-continued

| | pH 9.5: Impurities (%) | | | |
|---|---|---|---|---|
| | Without Autoclaving | | Autoclaved | |
| Trr | Glass 100 ml | Glass 200 ml | Glass 100 ml | Glass 200 ml |
| 0.20 | ND | ND | ND | ND |
| 0.31 (Imp N) | 0.06 | 0.06 | 0.06 | 0.06 |
| 0.58 | 0.02 | 0.01 | 0.02 | 0.02 |
| 0.93 (Imp A) | 0.02 | 0.02 | 0.02 | 0.02 |
| 1.83 | ND | ND | ND | ND |
| Total | 0.10 | 0.09 | 0.10 | 0.10 |

| | Without Autoclaving | | Autoclaved | |
|---|---|---|---|---|
| Trr | PE 100 ml | PE 200 ml | PE 100 ml | PE 200 ml |
| 0.20 (Imp J) | ND | ND | ND | ND |
| 0.31 (Imp N) | 0.06 | 0.06 | 0.06 | 0.06 |
| 0.58 | 0.02 | 0.02 | 0.02 | 0.02 |
| 0.93 (Imp A) | 0.02 | 0.02 | 0.02 | 0.02 |
| 1.83 | ND | ND | ND | ND |
| Total | 0.10 | 0.10 | 0.10 | 0.10 |

Again at pH of 9.5, the samples packaged in containers of glass and of PE show a practically unchanged content of impurities after autoclaving, whereas those packaged in containers of PVC and PP show, after said process, a smaller increment than at the previous pH values, changing on average from 0.10% to 0.11%.

Accordingly, it can be concluded that, after the autoclaving process, the increase in the content of impurities is smaller as the pH increases, which undoubtedly means an appreciable advantage for formulations intended for use in injection.

2) Investigation of the Ibuprofen Content of the Test Formulations after Autoclaving:

Without ignoring the relevance of other parameters such as the content of impurities, it is beyond doubt that for a pharmaceutical compositon for injection the content of ibuprofen after autoclaving is a very important parameter. For the present purposes, the minimum acceptable content of ibuprofen after autoclaving is considered to be at least 95% of the initial ibuprofen content added to the solution.

After autoclaving, the ibuprofen remaining in the formulations was determined by evaluating the loss produced by the autoclaving. Determination of ibuprofen was again based on analysis by HPLC using the following parameters:

Mobile phase: For preparation of the mobile phase, 6 g of trifluoroacetic acid was dissolved in 600 ml of water and was adjusted to pH=3 with dilute ammonium hydroxide; then 900 ml of acetonitrile was added.
Flow: 1 ml/min.
Column: C18, 150 mm×4.6 mm, 5 µm.
Detection: 254 nm.
Volume injected: 10 µl.
Temperature=25° C.
Duration=8 minutes.
Test sample: The test sample of ibuprofen is diluted to a concentration between 0.8 and 1.0 mg/ml.
Reference sample: Standard solution of ibuprofen in mobile phase at a concentration between 0.8 and 1.0 mg/ml.

The results are shown in the following table:

| pH | Material | Volume | Ibuprofen content % on 4 mg/ml (before autoclaving) | Ibuprofen content % on 4 mg/ml (after autoclaving) | Variation in the ibuprofen content (%) |
|---|---|---|---|---|---|
| 6.5 | PVC | 100 ml | 101.8 | 83.6 | −17.9% |
| | | 200 ml | 101.0 | 85.2 | −15.6% |
| | PP | 100 ml | 100.9 | 94.0 | −6.8% |
| | | 200 ml | 102.6 | 97.6 | −3.3% |
| | Glass | 100 ml | 102.7 | 92.0 | −10.4% |
| | | 200 ml | 101.6 | 93.5 | −8.0% |
| | PE | 100 ml | 100.3 | 94.5 | −5.8% |
| | | 200 ml | 99.8 | 96.4 | −3.4% |
| 7.0 | PVC | 100 ml | 102.8 | 89.8 | −12.6% |
| | | 200 ml | 103.2 | 93.6 | −9.3% |
| | PP | 100 ml | 103.0 | 97.9 | −5.0% |
| | | 200 ml | 101.0 | 99.4 | −1.6% |
| | Glass | 100 ml | 102.0 | 103.3 | +1.3% |
| | | 200 ml | 103.4 | 104.1 | +0.7% |
| | PE | 100 ml | 100.7 | 100.8 | +0.0% |
| | | 200 ml | 102.2 | 102.2 | +0.0% |
| 7.5 | PVC | 100 ml | 104.6 | 97.8 | −6.5% |
| | | 200 ml | 102.6 | 99.0 | −3.5% |
| | PP | 100 ml | 103.7 | 104.2 | +0.5% |
| | | 200 ml | 103.9 | 103.9 | +0.0% |
| | Glass | 100 ml | 102.7 | 101.5 | −1.2% |
| | | 200 ml | 100.8 | 101.2 | +0.4% |
| | PE | 100 ml | 102.3 | 98.9 | −3.3% |
| | | 200 ml | 102.1 | 103.3 | +1.2% |
| 7.8 | PVC | 100 ml | 102.1 | 97.9 | −4.1% |
| | PP | 100 ml | 102.7 | 99.4 | −3.2% |
| | Glass | 100 ml | 103.1 | 102.7 | −0.4% |
| | PE | 100 ml | 102.2 | 100.2 | −2.0% |

| pH | Material | Volume | Ibuprofen content % on 4 mg/ml (before autoclaving) | Ibuprofen content % on 4 mg/ml (after autoclaving) | Variation in the ibuprofen content (%) |
|---|---|---|---|---|---|
| 8.0 | PVC | 100 ml | 101.1 | 99.7 | −1.4% |
|  |  | 200 ml | 99.2 | 99.6 | +0.4% |
|  | PP | 100 ml | 100.8 | 95.9 | −4.9% |
|  |  | 200 ml | 100.2 | 102.4 | +2.2% |
|  | Glass | 100 ml | 102.9 | 104.7 | +1.7% |
|  |  | 200 ml | 102.3 | 101.6 | −0.1% |
|  | PE | 100 ml | 100.6 | 103.9 | +3.3% |
|  |  | 200 ml | 102.5 | 103.4 | +0.9% |
| 8.2 | PVC | 100 ml | 102.5 | 99.1 | −3.3% |
|  | PP | 100 ml | 102.0 | 100.5 | −1.5% |
|  | Glass | 100 ml | 102.5 | 99.1 | −3.3% |
|  | PE | 100 ml | 102.1 | 100.8 | −1.3% |
| 8.5 | PVC | 100 ml | 102.0 | 102.3 | +0.3% |
|  |  | 200 ml | 101.2 | 103.0 | +1.8% |
|  | PP | 100 ml | 101.9 | 103.7 | +1.8% |
|  |  | 200 ml | 102.1 | 102.3 | +0.2% |
|  | Glass | 100 ml | 101.1 | 101.1 | +0.0% |
|  |  | 200 ml | 101.1 | 101.4 | +0.3% |
|  | PE | 100 ml | 100.7 | 101.6 | +0.9% |
|  |  | 200 ml | 101.4 | 101.1 | −0.3% |
| 9.0 | PVC | 100 ml | 103.4 | 103.4 | +0.0% |
|  |  | 200 ml | 101.3 | 103.6 | +2.3% |
|  | PP | 100 ml | 103.5 | 103.9 | +0.4% |
|  |  | 200 ml | 100.2 | 103.9 | +3.7% |
|  | Glass | 100 ml | 100.1 | 104.8 | +4.7% |
|  |  | 200 ml | 101.0 | 100.4 | −0.6% |
|  | PE | 100 ml | 101.7 | 101.9 | +0.2% |
|  |  | 200 ml | 101.6 | 100.8 | −0.8% |
| 9.5 | PVC | 100 ml | 99.5 | 100.1 | +0.6% |
|  |  | 200 ml | 100.0 | 100.4 | +0.4% |
|  | PP | 100 ml | 100.0 | 100.6 | +0.6% |
|  |  | 200 ml | 99.9 | 100.7 | +0.8% |
|  | Glass | 100 ml | 100.8 | 101.5 | +0.7% |
|  |  | 200 ml | 100.9 | 99.2 | −1.7% |
|  | PE | 100 ml | 99.2 | 101.7 | +2.5% |
|  |  | 200 ml | 99.8 | 102.6 | +2.8% |

Just as in the case of impurities, we observe a tendency for a smaller loss of active principle (ibuprofen) to be obtained on increasing the pH, though to a varying extent depending on the container used. At pH of 6.5, loss of ibuprofen is increased in all cases. However, at pH 7.0 the loss of ibuprofen is already negligible in the samples packaged in glass and PE, whereas it is still significant in PP and, especially, PVC. At pH 7.5 the loss of ibuprofen is now only significant in PVC, and for pH greater than or equal to 8.0 the loss is not significant in any container.

On its side, the experimental tests carried out on the compositions produced according to the teachings of the DE document produced the following results:

| pH | Material | Volume | Ibuprofen content % on 4 mg/ml (before autoclaving) | Ibuprofen content % on 4 mg/ml (after autoclaving) | Variation in the ibuprofen content (%) |
|---|---|---|---|---|---|
| 7.0 | PVC | 100 ml | 90.5 | 72.0 | −20.4% |
|  | PP | 100 ml | 96.6 | 75.7 | −21.6% |
|  | Glass | 100 ml | 96.3 | 88.2 | −8.4% |
|  | PE | 100 ml | 95.4 | 91.7 | −3.9% |
| 7.8 | PVC | 100 ml | 93.9 | 78.4 | −16.5% |
|  | PP | 100 ml | 95.3 | 81.7 | −14.3% |
|  | Glass | 100 ml | 94.2 | 89.1 | −5.4% |
|  | PE | 100 ml | 94.7 | 92.2 | −2.6% |
| 8.2 | PVC | 100 ml | 94.8 | 85.3 | −10.0% |
|  | PP | 100 ml | 99.1 | 94.2 | −4.9% |
|  | Glass | 100 ml | 98.4 | 94.4 | −4.1% |
|  | PE | 100 ml | 98.6 | 94.7 | −3.9% |
| 9.0 | PVC | 100 ml | 99.3 | 88.2 | −11.2% |
|  | PP | 100 ml | 99.6 | 91.0 | −8.6% |
|  | Glass | 100 ml | 99.9 | 81.1 | −18.8% |
|  | PE | 100 ml | 99.8 | 94.4 | −5.4% |

As can be observed, in the compositions prepared according to the teachings of the DE document an incomplete ibuprofen dissolution was frequently observed already before autoclaving, with initial ibuprofen contents below the required 95% minimum value, and in one case even hardly reaching 90%. These results are even worser after autoclaving since, following this thermal treatment, in no case the required minimum ibuprofen content of 95% was reached, and in many cases loses higher than 5% were found. In conclusion, the compositions having an ibuprofen content of about 8 mg/ml and a trometamol content of about 6.05 mg/ml are not suitable for autoclaving and compositions so prepared may lose upon autoclaving up to 28% of the initial ibuprofen added, depending on the pH considered.

3) Investigation of the Change in pH of the Test Formulations after Autoclaving:

The pH of the test formulations was measured after packaging, either without autoclaving or after autoclaving, to evaluate the change in this parameter caused by said process. The results were as follows:

| pH | Material | Volume | Before autoclaving | After autoclaving |
|---|---|---|---|---|
| 6.5 | PVC | 100 ml | 7.44 | 7.80 |
|  |  | 200 ml | 7.43 | 7.75 |
|  | PP | 100 ml | 7.47 | 7.58 |
|  |  | 200 ml | 7.44 | 7.58 |
|  | Glass | 100 ml | 6.93 | 6.90 |
|  |  | 200 ml | 6.83 | 6.92 |
|  | PE | 100 ml | 6.66 | 7.50 |
|  |  | 200 ml | 6.64 | 7.42 |
| 7.0 | PVC | 100 ml | 7.91 | 8.03 |
|  |  | 200 ml | 7.89 | 8.01 |
|  | PP | 100 ml | 7.88 | 7.86 |
|  |  | 200 ml | 7.87 | 7.89 |
|  | Glass | 100 ml | 7.41 | 7.40 |
|  |  | 200 ml | 7.30 | 7.39 |
|  | PE | 100 ml | 7.25 | 7.58 |
|  |  | 200 ml | 7.26 | 7.54 |
| 7.5 | PVC | 100 ml | 8.37 | 8.39 |
|  |  | 200 ml | 8.35 | 8.40 |
|  | PP | 100 ml | 8.34 | 8.34 |
|  |  | 200 ml | 8.38 | 8.34 |
|  | Glass | 100 ml | 7.85 | 7.84 |
|  |  | 200 ml | 7.86 | 7.86 |
|  | PE | 100 ml | 7.72 | 7.91 |
|  |  | 200 ml | 7.75 | 7.89 |
| 8 | PVC | 100 ml | 8.74 | 8.72 |
|  |  | 200 ml | 8.73 | 8.72 |
|  | PP | 100 ml | 8.71 | 8.73 |
|  |  | 200 ml | 8.71 | 8.74 |
|  | Glass | 100 ml | 8.31 | 8.28 |
|  |  | 200 ml | 8.31 | 8.32 |
|  | PE | 100 ml | 8.22 | 8.29 |
|  |  | 200 ml | 8.21 | 8.28 |

-continued

| pH | Material | Volume | Before autoclaving | After autoclaving |
|---|---|---|---|---|
| 8.5 | PVC | 100 ml | 9.12 | 9.15 |
|  |  | 200 ml | 9.11 | 9.16 |
|  | PP | 100 ml | 9.11 | 9.16 |
|  |  | 200 ml | 9.06 | 9.11 |
|  | Glass | 100 ml | 8.70 | 8.77 |
|  |  | 200 ml | 8.73 | 8.79 |
|  | PE | 100 ml | 8.87 | 8.57 |
|  |  | 200 ml | 8.82 | 8.56 |
| 9.0 | PVC | 100 ml | 9.42 | 9.38 |
|  |  | 200 ml | 9.44 | 9.38 |
|  | PP | 100 ml | 9.46 | 9.44 |
|  |  | 200 ml | 9.47 | 9.42 |
|  | Glass | 100 ml | 9.23 | 9.14 |
|  |  | 200 ml | 9.21 | 9.24 |
|  | PE | 100 ml | 9.18 | 8.95 |
|  |  | 200 ml | 9.16 | 8.97 |
| 9.5 | PVC | 100 ml | 9.83 | 9.72 |
|  |  | 200 ml | 9.80 | 9.70 |
|  | PP | 100 ml | 9.76 | 9.64 |
|  |  | 200 ml | 9.77 | 9.67 |
|  | Glass | 100 ml | 9.62 | 9.64 |
|  |  | 200 ml | 9.67 | 9.65 |
|  | PE | 100 ml | 9.40 | 9.27 |
|  |  | 200 ml | 9.37 | 9.29 |

On comparing the formulations after packaging without autoclaving and autoclaved, it is seen that the effect is, once again, slightly different depending on the container used: In general, at pH=6.5 we observe a significant increase in pH after autoclaving, which is a clear indication of the degradation of some of the components of the formulation, giving rise to derivatives of an alkaline character. However, this increase in pH is very significant in the samples stored in PE, is less significant in the samples stored in PVC and PP, and is hardly observed at all in the samples stored in glass. Moreover, as the initial pH of the formulations tested is increased, this increase in pH after autoclaving gradually decreases, so that it is hardly observed at all at certain pH values depending on the container used: The formulations in which the samples in the different containers have a barely observable decrease in pH are:

for glass, starting from pH=6.5 for PP, starting from pH=7.0, and for PVC, starting from pH=7.5, whereas for PE said increase, although it is reduced to values of the order of 0.1 units of pH at pH values of about 9.5, can never be regarded as barely observable.

4) Investigation of Sub-Visible Particles:

The sub-visible particles in the formulations were also measured before and after autoclaving. This investigation was performed by direct measurement of this parameter in the sub-visible particle counter. The specification according to the European Pharmacopoeia is as follows:

For 100 ml:

≤6000 part./container≥10 μm

≤600 part./container≥25 μm

For 200 ml:

≤25 part./ml≥10 μm

≤3 part./ml≥25 μm

The results obtained in the formulations tested were as follows:

| pH | Material | Volume | Without Autoclaving | Autoclaved |
|---|---|---|---|---|
| 6.5 | PVC | 100 ml | 556 part./bag ≥ 10 μm | 1122 part./bag ≥ 10 μm |
|  |  |  | 100 part./bag ≥ 25 μm | 67 part./bag ≥ 25 μm |
|  |  | 200 ml | 4 part./ml ≥ 10 μm | 16 part./ml ≥ 10 μm |
|  |  |  | 0 part./ml ≥ 25 μm | 1 part./ml ≥ 25 μm |
|  | PP | 100 ml | 489 part./bag ≥ 10 μm | 300 part./bag ≥ 10 μm |
|  |  |  | 89 part./bag ≥ 25 μm | 33 part./bag ≥ 25 μm |
|  |  | 200 ml | 4 part./ml ≥ 10 μm | 2 part./ml ≥ 10 μm |
|  |  |  | 1 part./ml ≥ 25 μm | 0 part./ml ≥ 25 μm |
|  | Glass | 100 ml | 889 part./container ≥ 10 μm | 411 part./container ≥ 10 μm |
|  |  |  | 167 part./container ≥ 25 μm | 67 part./container ≥ 25 μm |
|  |  | 200 ml | 4 part./ml ≥ 10 μm | 8 part./ml ≥ 10 μm |
|  |  |  | 1 part./ml ≥ 25 μm | 1 part./ml ≥ 25 μm |
|  | PE | 100 ml | 2544 part./container ≥ 10 μm | 2967 part./container ≥ 10 μm |
|  |  |  | 67 part./container ≥ 25 μm | 589 part./container ≥ 25 μm |
|  |  | 200 ml | 11 part./ml ≥ 10 μm | 12 part./ml ≥ 10 μm |
|  |  |  | 1 part./ml ≥ 25 μm | 1 part./ml ≥ 25 μm |
| 7 | PVC | 100 ml | 533 part./bag ≥ 10 μm | 411 part./bag ≥ 10 μm |
|  |  |  | 156 part./bag ≥ 25 μm | 67 part./bag ≥ 25 μm |
|  |  | 200 ml | 6 part./ml ≥ 10 μm | 5 part./ml ≥ 10 μm |
|  |  |  | 0 part./ml ≥ 25 μm | 2 part./ml ≥ 25 μm |
|  | PP | 100 ml | 389 part./bag ≥ 10 μm | 667 part./bag ≥ 10 μm |
|  |  |  | 78 part./bag ≥ 25 μm | 33 part./bag ≥ 25 μm |
|  |  | 200 ml | 2 part./ml ≥ 10 μm | 5 part./ml ≥ 10 μm |
|  |  |  | 1 part./ml ≥ 25 μm | 1 part./ml ≥ 25 μm |
|  | Glass | 100 ml | 467 part./container ≥ 10 μm | 922 part./container ≥ 10 μm |
|  |  |  | 78 part./container ≥ 25 μm | 89 part./container ≥ 25 μm |
|  |  | 200 ml | 9 part./ml ≥ 10 μm | 4 part./ml ≥ 10 μm |
|  |  |  | 1 part./ml | 0 part./ml ≥ 25 μm |
|  | PE | 100 ml | 1322 part./container ≥ 10 μm | 4733 part./container ≥ 10 μm |
|  |  |  | 100 part./container ≥ 25 μm | 500 part./container ≥ 25 μm |
|  |  | 200 ml | 15 part./ml ≥ 10 μm | 15 part./ml ≥ 10 μm |
|  |  |  | 1 part./ml ≥ 25 μm | 2 part./ml ≥ 25 μm |

-continued

| pH | Material | Volume | Without Autoclaving | Autoclaved |
|---|---|---|---|---|
| 7.5 | PVC | 100 ml | 522 part./bag ≥ 10 μm<br>67 part./bag ≥ 25 μm | 3189 part./bag ≥ 10 μm<br>322 part./bag ≥ 25 μm |
| | | 200 ml | 7 part./ml ≥ 10 μm<br>1 part./ml ≥ 25 μm | 10 part./ml ≥ 10 μm<br>0 part./ml ≥ 25 μm |
| | PP | 100 ml | 456 part./bag ≥ 10 μm<br>44 part./bag ≥ 25 μm | 933 part./bag ≥ 10 μm<br>56 part./bag ≥ 25 μm |
| | | 200 ml | 3 part./ml ≥ 10 μm<br>0 part./ml ≥ 25 μm | 4 part./ml ≥ 10 μm<br>0 part./ml ≥ 25 μm |
| | Glass | 100 ml | 911 part./container ≥ 10 μm<br>133 part./container ≥ 25 μm | 156 part./container ≥ 10 μm<br>11 part./container ≥ 25 μm |
| | | 200 ml | 6 part./ml ≥ 10 μm<br>1 part./ml ≥ 25 μm | 3 part./ml ≥ 10 μm<br>0 part./ml ≥ 25 μm |
| | PE | 100 ml | 2033 part./container ≥ 10 μm<br>122 part./container ≥ 25 μm | 1022 part./container ≥ 10 μm<br>56 part./container ≥ 25 μm |
| | | 200 ml | 23 part./ml ≥ 10 μm<br>1 part./ml ≥ 25 μm | 22 part./ml ≥ 10 μm<br>2 part./ml ≥ 25 μm |
| 8 | PVC | 100 ml | 500 part./bag ≥ 10 μm<br>89 part./bag ≥ 25 μm | 544 part./bag ≥ 10 μm<br>44 part./bag ≥ 25 μm |
| | | 200 ml | 3 part./ml ≥ 10 μm<br>0 part./ml ≥ 25 μm | 13 part./ml ≥ 10 μm<br>1 part./ml ≥ 25 μm |
| | PP | 100 ml | 400 part./bag ≥ 10 μm<br>44 part./bag ≥ 25 μm | 222 part./bag ≥ 10 μm<br>33 part./bag ≥ 25 μm |
| | | 200 ml | 6 part./ml ≥ 10 μm<br>0 part./ml ≥ 25 μm | 2 part./ml ≥ 10 μm<br>0 part./ml ≥ 25 μm |
| | Glass | 100 ml | 2367 part./container ≥ 10 μm<br>111 part./container ≥ 25 μm | 444 part./container ≥ 10 μm<br>22 part./container ≥ 25 μm |
| | | 200 ml | 6 part./ml ≥ 10 μm<br>1 part./ml ≥ 25 μm | 2 part./ml ≥ 10 μm<br>0 part./ml ≥ 25 μm |
| | PE | 100 ml | 667 part./container ≥ 10 μm<br>56 part./container ≥ 25 μm | 2300 part./container ≥ 10 μm<br>22 part./container ≥ 25 μm |
| | | 200 ml | 13 part./ml ≥ 10 μm<br>2 part./ml ≥ 25 μm | 12 part./ml ≥ 10 μm<br>1 part./ml ≥ 25 μm |
| 8.5 | PVC | 100 ml | 444 part./bag ≥ 10 μm<br>33 part./bag ≥ 25 μm | 978 part./bag ≥ 10 μm<br>44 part./bag ≥ 25 μm |
| | | 200 ml | 5 part./ml ≥ 10 μm<br>1 part./ml ≥ 25 μm | 7 part./ml ≥ 10 μm<br>1 part./ml ≥ 25 μm |
| | PP | 100 ml | 222 part./bag ≥ 10 μm<br>67 part./bag ≥ 25 μm | 467 part./bag ≥ 10 μm<br>44 part./bag ≥ 25 μm |
| | | 200 ml | 2 part./ml ≥ 10 μm<br>0 part./ml ≥ 25 μm | 4 part./ml ≥ 10 μm<br>0 part./ml ≥ 25 μm |
| | Glass | 100 ml | 978 part./container ≥ 10 μm<br>111 part./container ≥ 25 μm | 267 part./container ≥ 10 μm<br>44 part./container ≥ 25 μm |
| | | 200 ml | 6 part./ml ≥ 10 μm<br>0 part./ml ≥ 25 μm | 2 part./ml ≥ 10 μm<br>0 part./ml ≥ 25 μm |
| | PE | 100 ml | 722 part./container ≥ 10 μm<br>100 part./container ≥ 25 μm | 1656 part./container ≥ 10 μm<br>167 part./container ≥ 25 μm |
| | | 200 ml | 4 part./ml ≥ 10 μm<br>1 part./ml ≥ 25 μm | 9 part./ml ≥ 10 μm<br>1 part./ml ≥ 25 μm |
| 9 | PVC | 100 ml | 344 part./bag ≥ 10 μm<br>89 part./bag ≥ 25 μm | 2689 part./bag ≥ 10 μm<br>100 part./bag ≥ 25 μm |
| | | 200 ml | 4 part./ml ≥ 10 μm<br>0 part./ml ≥ 25 μm | 37 part./ml ≥ 10 μm<br>1 part./ml ≥ 25 μm |
| | PP | 100 ml | 667 part./bag ≥ 10 μm<br>89 part./bag ≥ 25 μm | 1200 part./bag ≥ 10 μm<br>56 part./bag ≥ 25 μm |
| | | 200 ml | 3 part./ml ≥ 10 μm<br>0 part./ml ≥ 25 μm | 16 part./ml ≥ 10 μm<br>2 part./ml ≥ 25 μm |
| | Glass | 100 ml | 800 part./container ≥ 10 μm<br>67 part./container ≥ 25 μm | 278 part./container ≥ 10 μm<br>44 part./container ≥ 25 μm |
| | | 200 ml | 3 part./ml ≥ 10 μm<br>0 part./ml ≥ 25 μm | 2 part./ml ≥ 10 μm<br>0 part./ml ≥ 25 μm |
| | PE | 100 ml | 1978 part./container ≥ 10 μm<br>211 part./container ≥ 25 μm | 2722 part./container ≥ 10 μm<br>4 part./container ≥ 25 μm |
| | | 200 ml | 8 part./ml ≥ 10 μm<br>1 part./ml ≥ 25 μm | 14 part./ml ≥ 10 μm<br>2 part./ml ≥ 25 μm |
| 9.5 | PVC | 100 ml | 611 part./bag ≥ 10 μm<br>133 part./bag ≥ 25 μm | 28756 part./bag ≥ 10 μm<br>4456 part./bag ≥ 25 μm(*1) |
| | | 200 ml | 16 part./ml ≥ 10 μm<br>2 part./ml ≥ 25 μm | 721 part./ml ≥ 10 μm<br>119 part./ml ≥ 25 μm(*1) |
| | PP | 100 ml | 789 part./bag ≥ 10 μm<br>100 part./bag ≥ 25 μm | 3878 part./bag ≥ 10 μm<br>878 part./bag ≥ 25 μm(*1) |
| | | 200 ml | 3 part./ml ≥ 10 μm<br>0 part./ml ≥ 25 μm | 18 part./ml ≥ 10 μm<br>3 part./ml ≥ 25 μm(*1) |
| | Glass | 100 ml | 989 part./container ≥ 10 μm<br>44 part./container ≥ 25 μm | 389 part./container ≥ 10 μm<br>0 part./container ≥ 25 μm |
| | | 200 ml | 6 part./ml ≥ 10 μm<br>1 part./ml ≥ 25 μm | 2 part./ml ≥ 10 μm<br>0 part./ml ≥ 25 μm |

-continued

| pH | Material | Volume | Without Autoclaving | Autoclaved |
|---|---|---|---|---|
| | PE | 100 ml | 1189 part./container ≥ 10 μm<br>144 part./container ≥ 25 μm | 1911 part./container ≥ 10 μm<br>111 part./container ≥ 25 μm |
| | | 200 ml | 10 part./ml ≥ 10 μm<br>1 part./ml ≥ 25 μm | 14 part./ml ≥ 10 μm<br>2 part./ml ≥ 25 μm |

(*1) A large amount of particles and filaments, visible in suspension, appears.

It can be seen in this table that when the formulations are packaged in glass containers, in all cases the level of sub-visible particles is within the specifications, and with a slight tendency to exhibit a lower level of said particles on increasing the pH of the formulation, particularly in the case of the formulations that are autoclaved, although it is in any case concluded that for glass the acceptable pH range of the formulations comprises all the pH values tested, i.e. from 6.5 to 9.5.

However, in the case of formulations packaged in PP, in PVC and in PE, high pH levels (pH=9.5) give rise to an increased amount of sub-visible particles in the case of the autoclaved formulations, particularly in the case of PVC, and to a smaller extent PP and PE. Therefore in the case of these materials, the acceptable pH range of the formulations would comprise from 6.5 to 9.0.

Accordingly, it can be concluded that although the formulations of ibuprofen for injection according to the invention can be used, in general, between pH of 7.0 and 9.5, the most preferred embodiments of the invention would be, for example, the following:

When the formulation is in containers of glass: pH of the formulation between 7.0 and 9.5, more preferably between 8.0 and 9.0 and most preferably about 8.5;

When the formulation is in containers of PE: pH of the formulation between 7.0 and 9.0, more preferably between 8.0 and 9.0 and most preferably about 8.5;

When the formulation is in containers of PP: pH of the formulation between 7.5 and 9.0; more preferably between 8.0 and 9.0, and most preferably about 8.5;

When the formulation is in containers of PVC: pH of the formulation between 8.0 and 9.0, and more preferably about 8.5.

These formulations are able to maintain the levels of concentration of the active principle within acceptable values after autoclaving, with an acceptable variation of other important parameters of the compositions such as increase in content of impurities, change in pH or increase in sub-visible particles when the formulations of the invention are submitted to autoclaving.

The invention claimed is:

1. Pharmaceutical composition of ibuprofen for njection comprising an aqueous solution of ibuprofen and trometamol, wherein the concentration of ibuprofen is between 2 and 6 mg/ml, the concentration of trometamol is 3.8 mg/ml, and the pH is between 7.0 and 9.5.

2. Pharmaceutical composition of ibuprofen for injection according to claim 1, wherein the concentration of ibuprofen is about 4 mg/ml.

3. Pharmaceutical composition according to claim 1, which is sterilizable by heat by autoclaving at a temperature between 110° C. and 130° C. for a time between 2 and 190 minutes.

4. Pharmaceutical composition according to claim 3, wherein the composition is sterilizable by heat by autoclaving at a temperature of 121° C. for 15 minutes.

5. Pharmaceutical composition of ibuprofen for injection according to claim 1, wherein, when the composition is provided in containers of glass, the pH is between 7.0 and 9.5.

6. Pharmaceutical composition of ibuprofen for injection according to claim i when the composition is provided in containers of polyethylene, the pH is between 7.0 and 9.0.

7. Pharmaceutical composition of ibuprofen for injection according to claim 1, wherein, when the composition is provided in containers of polypropylene, the pH is between 7.5 and 9.0.

8. Pharmaceutical composition of ibuprofen for injection according to claim 1, wherein when the composition is provided in containers of PVC, the pH is between 8.0 and 9.0.

9. Pharmaceutical composition according to claim 1, wherein the pH is about 8.5.

10. Pharmaceutical composition according to claim 1, further comprising a salt in the necessary amount for endowing the composition with an osmolality of about 300 mOsm/kg.

11. Pharmaceutical composition according to claim 10, wherein the salt is NaCl at a concentration of approximately 7.7 mg/ml.

12. Composition according to claim 1, for use in the treatment of pain, inflammation or fever.

13. Composition according to claim 12, which is provided in containers of 100 ml or 200 ml.

14. Method of treatment of pain, inflammation or fever which comprises administering to a patient in need thereof a therapeutically effective amount of a pharmaceutical composition according to claim 1.

* * * * *